(12) United States Patent
Som et al.

(10) Patent No.: US 10,897,905 B2
(45) Date of Patent: Jan. 26, 2021

(54) HYPOCHLORITE BASED HARD SURFACE DISINFECTANTS

(71) Applicant: Metrex Research, LLC, Orange, CA (US)

(72) Inventors: Abhigyan Som, Brea, CA (US); Olga Borokhov, Torrance, CA (US); Timothy J. Taylor, Orange, CA (US); Harish Jani, Lake Forest, CA (US); Anabell Jackson, Placentia, CA (US); Robert Carrier, Moreno Valley, CA (US)

(73) Assignee: METREX RESEARCH, LLC, Orange, CA (US)

( * ) Notice: Subject to any disclaimer, the term of this patent is extended or adjusted under 35 U.S.C. 154(b) by 29 days.

(21) Appl. No.: 15/415,269

(22) Filed: Jan. 25, 2017

(65) Prior Publication Data

US 2017/0208812 A1 Jul. 27, 2017

Related U.S. Application Data

(60) Provisional application No. 62/287,031, filed on Jan. 26, 2016.

(51) Int. Cl.

| | |
|---|---|
| *A01N 59/00* | (2006.01) |
| *A01N 25/10* | (2006.01) |
| *A61L 2/18* | (2006.01) |
| *A01N 25/02* | (2006.01) |
| *A61K 33/20* | (2006.01) |
| *A61L 2/00* | (2006.01) |
| *A61L 2/22* | (2006.01) |

(52) U.S. Cl.
CPC ............ *A01N 59/00* (2013.01); *A01N 25/02* (2013.01); *A01N 25/10* (2013.01); *A61K 33/20* (2013.01); *A61L 2/0088* (2013.01); *A61L 2/18* (2013.01); *A61L 2/22* (2013.01); *A61L 2202/15* (2013.01)

(58) Field of Classification Search
CPC ..................................................... A01N 59/00
See application file for complete search history.

(56) References Cited

U.S. PATENT DOCUMENTS

| | | | |
|---|---|---|---|
| 3,749,672 A | 7/1973 | Golton et al. | |
| 5,462,689 A | 10/1995 | Choy et al. | |
| 5,821,214 A | 10/1998 | Weibel | |
| 5,908,707 A * | 6/1999 | Cabell | C11D 17/049 |
| | | | 424/405 |
| 6,022,840 A | 2/2000 | Weibel | |
| 6,036,789 A | 3/2000 | Weibel | |
| 6,162,371 A | 12/2000 | Rees et al. | |
| 6,448,215 B1 | 9/2002 | Grande et al. | |
| 6,471,974 B1 | 10/2002 | Rees et al. | |
| 6,649,581 B1 | 11/2003 | Lalle et al. | |
| 6,825,159 B2 | 11/2004 | Man et al. | |
| 6,827,792 B2 | 12/2004 | Cervero et al. | |
| 6,998,379 B1 | 2/2006 | Costagliola | |
| 7,008,600 B2 † | 3/2006 | Katsigras | |
| 7,070,737 B2 † | 7/2006 | Bains | |
| 7,390,775 B2 | 6/2008 | Rees et al. | |
| 7,592,301 B2 * | 9/2009 | Smith | C11D 1/02 |
| | | | 510/180 |
| 7,967,220 B2 | 6/2011 | Hansen et al. | |
| 8,318,654 B2 | 11/2012 | Hoffman et al. | |
| 8,765,114 B2 | 7/2014 | Scheuing et al. | |
| 8,894,907 B2 | 11/2014 | Privitera et al. | |
| 2003/0155549 A1 | 8/2003 | Yoshikawa et al. | |
| 2005/0008576 A1 | 1/2005 | Makansi | |
| 2005/0025668 A1 * | 2/2005 | Katsigras | A01N 59/00 |
| | | | 422/37 |
| 2005/0202491 A1 | 9/2005 | Nelson et al. | |
| 2005/0282722 A1 | 12/2005 | McReynolds et al. | |
| 2006/0089285 A1 | 4/2006 | Ahmed et al. | |
| 2006/0278586 A1 | 12/2006 | Nalepa et al. | |
| 2007/0231247 A1 * | 10/2007 | Bromberg | A61L 2/18 |
| | | | 423/473 |
| 2009/0016990 A1 | 1/2009 | Alberte et al. | |
| 2009/0050179 A1 | 2/2009 | Kang et al. | |
| 2011/0045187 A1 * | 2/2011 | McCloskey | D04H 1/02 |
| | | | 427/294 |
| 2013/0216293 A1 * | 8/2013 | Garner | B65D 25/08 |
| | | | 401/34 |
| 2013/0280349 A1 | 10/2013 | Kimler et al. | |
| 2014/0117278 A1 | 5/2014 | Cawlfield et al. | |
| 2014/0134224 A1 | 5/2014 | Mallet et al. | |
| 2014/0328946 A1 | 11/2014 | Northey | |
| 2015/0030528 A1 | 1/2015 | Ku | |

FOREIGN PATENT DOCUMENTS

| | | | |
|---|---|---|---|
| CA | 2028930 A1 | | 5/1992 |
| EP | 1281320 | | 2/2003 |
| EP | 1550468 | | 7/2005 |
| WO | WO 8805462 | * | 1/1988 |
| WO | 97/43392 | | 11/1997 |
| WO | 98/11776 | | 3/1998 |
| WO | 2004108091 | | 12/2004 |
| WO | 2010046142 | | 4/2010 |
| WO | 2013032961 | | 3/2013 |

(Continued)

OTHER PUBLICATIONS

PCT/US2017/015050 International Search Report and Written Opinion of the International Searching Authority dated Mar. 29, 2017 (17 pages).

(Continued)

*Primary Examiner* — Sarah Alawadi

(74) *Attorney, Agent, or Firm* — Michael Best & Friedrich LLP

(57) ABSTRACT

A disinfectant includes a source of chlorine, a buffer system, a pH adjuster, and a polar carrier. The disinfectant has a pH of 9.9-11 and activity against *Clostridium difficile* spores and *Mycobacterium* within a 3 minute kill time. In one embodiment, the disinfectant includes sodium hypochlorite as a source of chlorine, a carbonate or phosphate buffer system, a hydroxide pH adjuster, and a polar carrier, wherein the disinfectant has a pH of 10.0-10.5 and kills at least 90% of *Clostridium difficile* spores and *Mycobacterium* within a 3 minute kill time.

24 Claims, No Drawings

(56) References Cited

FOREIGN PATENT DOCUMENTS

WO    2013171343    11/2013
WO    2014127713    8/2014

OTHER PUBLICATIONS

Rutala et al., "Uses of Inorganic Hypochlorite (Bleach) in Health-Care Facilities," clinical microbiology review (1997) vol. 10, No. 4, pp. 597-610, http://rutalapdf.web.unc.edu/files/2015/08/Rutalal-1997-Uses-of-inorganic-hypochlorite-bl.pdf.
International Preliminary Report on Patentability for Application No. PCT/US2017/015050 dated Aug. 9, 2018 (11 pages).
Clorox Germicidal Wipes Label Copyright 2007.†
Clorox Healthcare Bleach Germicidal Wipes Label Copyright 2013.†
EPA, EPA Registration No. 67619-12, Amendment Acceptance dated Jun. 21, 2012, 16 pages, https://www3.epa.gov/pesticides/chem_search/ppls/067619-00012-20120621.pdf.†
The Clorox Company "Ingredients Inside—Bleach Germicidal Wipes" retrieved Nov. 9, 2017 at https://www.thecloroxcompany.com/?ii_product=clorox-healthcare-bleach-germicidal-wipes-44600305776.†
National Silicates "N Sodium Silicate Solution" Apr. 5, 2012, 5 pages, https://www.pqcorp.com/docs/default-source/pq-corporation/sodium-silicate-liquids/n/n_sodium_silicate_msds2012.pdf?sfvrsn=62a0e578_.†

\* cited by examiner
† cited by third party

HYPOCHLORITE BASED HARD SURFACE DISINFECTANTS

TECHNICAL FIELD

The present invention relates to formulations for disinfecting surfaces. In particular, the present invention relates to buffered hypochlorite based hard surface disinfectants.

BACKGROUND

Microbial infection is a significant healthcare problem. Indeed, by some estimates, the incidence of hospital-acquired infection is around 1 out of each 25 patients. Not surprisingly, treatment clinics and hospitals contain many surfaces that tend to harbor the microbes responsible for infection and must be thoroughly sanitized often.

One pathogenic microbe in particular, *Clostridium difficile* ("*C. diff.*") spores, presents a high risk of infectious diarrhea among the patient population. Once a person has *C. diff.* infection, the infection can spread to others, because *C. diff.* spores exist in the feces of an infected person and can live on dry surfaces for a significant amount of time. A person who touches one of those surfaces can contract the infection. Thus, the first line of defense against microbial infection is the treatment of such surfaces with disinfectants.

Additionally, these surfaces containing *C. diff.* likely also contain additional pathogens, such as *Mycobacterium tuberculosis*, multidrug resistant bacteria, viruses, and fungi. Therefore, surface disinfectants should also exhibit activity against these other pathogens. To date, ready-to-use formulations containing hypochlorite have shown some effectiveness against *C. diff.*, but these formulations, under certain test conditions, typically exhibit a compromised activity against other pathogens, such as *Mycobacterium tuberculosis*.

In view of the above, there is a need for hypochlorite-based hard surface disinfectants, as either soaks or sprays or delivered on a substrate, that exhibit strong activity against *C. diff.* while maintaining activity against certain alternative pathogens, like *Mycobacterium*.

SUMMARY

In accordance with an embodiment of the invention, a disinfectant is provided. The disinfectant includes a source of chlorine, a buffer system, a pH adjuster, and a polar carrier. The disinfectant has a pH of 9.9-11 and activity against *Clostridium difficile* spores and *Mycobacterium* within a 3 minute kill time. A method of use and a disinfectant article are further provided.

In accordance with another embodiment of the invention, the disinfectant comprises sodium hypochlorite as a source of chlorine, a carbonate or phosphate buffer system, a hydroxide pH adjuster, and a polar carrier, wherein the disinfectant has a pH of 10.0-10.5 and kills at least 99.99% of *Clostridium difficile* spores and *Mycobacterium* within a 3 minute kill time.

DETAILED DESCRIPTION

In the discussion that follows, all concentrations are based on the total weight of the specified composition, unless stated otherwise. Weight percent, weight %, wt. %, percent by weight, and % by weight are synonyms that refer to the concentration of a substance as the weight of that substance, divided by the weight of the composition, and multiplied by 100.

In accordance with embodiments of the present invention, a hypochlorite-based hard surface disinfectant is provided. The disinfectant provides activity against *C. diff.* spores, pathogens associated with tuberculosis, such as *Mycobacterium terrae* and *bovis* (collectively "*Mycobacterium*"), other harmful bacteria, fungi, and certain viruses, all within a 3 minute kill time. The disinfectant may be in the form of a soak or spray or be provided on a substrate, such as a wipe. More particularly, the disinfectant includes a source of chlorine, a buffer system, a pH adjuster, and a polar carrier. The disinfectant has a shelf life of one year or more with retained biocidal efficacy.

The disinfectant includes a source of chlorine. For example, the disinfectant may include a hypochlorite, a chlorinated phosphate, a chlorinated isocyanurate, a chlorinated melamine, a chlorinated amide, or mixtures thereof. If a hypochlorite is used in the disinfectant, the hypochlorite may be added in the form of a salt with one or more different counterions, such as calcium, sodium, or potassium.

In particular, the source of chlorine may include sodium hypochlorite, potassium hypochlorite, calcium hypochlorite, lithium hypochlorite, chlorinated trisodiumphosphate, sodium dichloroisocyanurate, potassium dichloroisocyanurate, pentaisocyanurate, trichloromelamine, sulfondichloroamide, 1,3-dichloro-5,5-dimethyl hydantoin, N-chlorosuccinimide, N,N'-dichloroazodicarbonimide, N,N'-chloroacetylurea, N,N'-dichloro biuret, trichlorocyanuric acid and hydrates thereof, or combinations or mixtures thereof.

The source of chlorine is included within the composition in an amount sufficient to provide the desired level of available chlorine. For instance, a desired level of available chlorine may be from 0.1% to 10% available chlorine or from 0.5% to 5% available chlorine or from 0.8% to 2% available chlorine or 1% to 1.3% available chlorine. To attain the desired level of available chlorine, in at least some embodiments, the source of chlorine may be present in the range of about 0.5% to about 20%, or about 1% to about 19%, or about 5% to about 15%, or about 9% to about 12% by weight based on the total weight of a particular cleaning composition. For example, the source of chlorine may be present in an amount of about 0.5%, 1%, 2%, 3%, 4%, 5%, 6%, 7%, 8%, 9%, 10%, 11%, 12%, 13%, 14%, 15%, 16%, 17%, 18%, 19%, 20%, or any fractional part thereof. It should be understood that these ranges can vary, depending, for example, upon factors such as the desired level of available chlorine, and the desired level of chlorine stability.

Without intending to be bound by any particular theory, it is believed that the stability of the source of chlorine is affected by the level of alkalinity in the disinfectant. For example, in aqueous solutions of sodium hypochlorite, the solution will exist in the equilibrium indicated in formula (I) below. The equilibrium is affected by the pH of the solution. At high pH, the equilibrium favors hypochlorite ion (OCl⁻), but at low pH, the equilibrium favors molecular chlorine ($Cl_2$) and hypochlorous acid (HOCl).

$$Cl_2 + H_2O \leftrightharpoons HOCl \leftrightharpoons OCl^- + H_2O \qquad (I)$$

Among all the chlorine species present in an aqueous hypochlorite solution, hypochlorous acid is the strongest oxidant under standard conditions, and thus, is believed to be the most efficacious against microorganisms. Therefore, a hypochlorite solution should be more efficacious against microorganisms at lower pH values, below 9.0 for instance.

However, dilute hypochlorite solutions, in which there is 1.0% to 1.3% available chlorine, for instance, are unstable and demonstrate a rapid degradation at pH values below 11. It is believed that this degradation is caused by an unfavorable equilibrium shift toward unstable hypochlorous acid. However, this unstable hypochlorous acid may be stabilized through the addition of appropriate buffers, so that the pH level of a dilute disinfectant solution may be maintained at 11 or lower.

Thus, the disinfectant includes a buffer system. Buffers may include a silicate salt, a phosphate salt, a polyphosphate salt, a carbonate salt, a borate salt, or the like, or combinations or mixtures thereof. For instance, suitable buffers include sodium silicate, sodium metasilicate, sodium orthosilicate, sodium phosphate, sodium polyphosphate, sodium borate, sodium carbonate, sodium bicarbonate, potassium silicate, potassium metasilicate, potassium orthosilicate, potassium phosphate, potassium polyphosphate, potassium borate, potassium carbonate, potassium bicarbonate, lithium silicate, lithium metasilicate, lithium orthosilicate, lithium phosphate, lithium polyphosphate, lithium borate, lithium carbonate, or the like, or combinations or mixtures thereof.

In addition, the disinfectant may include a pH adjuster, such as a fully ionizable source of alkalinity. Exemplary fully ionizable sources of alkalinity include alkali metal hydroxides and alkaline earth metal hydroxides. For instance, suitable fully ionizable sources of alkalinity include lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, and mixtures thereof. Alternatively, the disinfectant may include a pH adjuster that is a fully ionizable source of acidity, such as a hydrohalic acid, sulfuric acid, nitric acid, or the like, or combinations or mixtures thereof.

The amount of the buffer and pH adjuster added may depend upon the desired level of alkalinity. As a measurement of the level of alkalinity in the disinfectant, the pH of the disinfectant may range from 9.9 to 11, or from 10.0 to 10.7, or from 10.0 to 10.5. For instance, the pH may be 9.9, 10.0, 10.1, 10.2, 10.3, 10.4, 10.5, 10.6, 10.7, 10.8, 10.9, 11.0, or any fractional part thereof. To achieve the desired pH level, the amount of buffer and pH adjuster may range from about 1% to about 10%. For instance, the total amount of buffer and pH adjuster may be about 0.5%, 1%, 2%, 3%, 4%, 5%, 6%, 7%, 8%, 9%, 10%, or any fractional part thereof.

The disinfectant also includes a polar carrier. An appropriate polar carrier is any polar solvent that is compatible with chlorine and the source of alkalinity. For instance, the polar carrier may be water.

When added to the weight percent values of all other components of the disinfectant, the concentration of the polar carrier should take that sum to 100%. Indeed, the amount of polar carrier may range from 10% to about 99%, or from about 20% to about 98%, or from about 30% to about 97%, or from about 40% to about 96%, or from about 50% to about 95%, or from about 60% to about 94%, or from about 70% to about 93%, or from about 80% to about 92%. For instance, the amount of polar carrier may be 81%, 82%, 83%, 84%, 85%, 86%, 87%, 88%, 89%, 90%, 91%, 92%, 93%, 94%, 95%, 96%, 97%, 98%, or any fractional part thereof.

In addition, the disinfectant may include other, optional ingredients. For example, the disinfectant may include one or more bleach compatible fragrances, one or more bleach compatible corrosion inhibitors, one or more bleach compatible chelating agents, and/or one or more bleach compatible surfactants. One of ordinary skill in the art is capable of selecting the appropriate additional ingredients and the concentrations thereof based upon the intended final application of the disinfectant.

The disinfectant may be in the form of a soak or spray or be provided on a substrate, such as a wipe. Suitable substrates may be provided by a variety of sources, including woven and non-woven webs, fabrics, foams, sponges, and similar material constructs capable of absorbing the liquid disinfectant composition. Generally, the absorbent carrier is preferred to be in sheet form, that is, in a form in which the cross-sectional thickness dimension of the absorbent carrier is proportionally smaller than either its approximate width or length dimension in order to provide at least one surface whose surface area is sized appropriately with respect to the intended surface to be treated with the disinfectant article. The absorbent carrier may be formed into individual sheets or wipes, or a continuous sheet, preferably with some separation means provided, such as partial tears or perforations across at least one dimension of the sheet, such that the sheet may be subdivided prior to use to a suitable size for the particular need.

Suitable substrates are generally selected from natural and synthetic materials, and include all suitable substrates that are bleach stable, in that they undergo no significant degradation or no significant chemical or physical change in structure, properties, or form, by contact with the components of the disinfectant. The substrate may include a single polymer or a mixture of two or more polymers. Suitable materials generally include synthetic polymer substrates, such as polyethylene terephthalate (PET), polyester (PE), high density polyethylene (HDPE), polyvinyl chloride (PVC), chlorinated polyvinylidene chloride (CPVC), polyacrylamide (ACAM), polystyrene (PS), polypropylene (PP), polycarbonate (PC), polyaryletherketone (PAEK), poly(cyclohexylene dimethylene cyclohexanedicarboxylate) (PCCE), poly(cyclohexylene dimethylene terephthalate) (PCTA), poly(cyclohexylene dimethylene terephthalate) glycol (PCTG), polyetherimide (PEI), polyethersulfone (PES), poly(ethylene terephthalate) glycol (PETG), polyketone (PK), poly(oxymethylene); polyformaldehyde (POMF), poly(phenylene ether) (PPE), poly(phenylene sulfide) (PPS), poly(phenylene sulfone) (PPSU), syndiotactic polystyrene (syn-PS), polysulfone (PSU), polytetrafluoroethylene (PTFE), polyurethane (PUR), poly(vinylidene fluoride) (PVDF), polyamide thermoplastic elastomer (TPA), polybutylene (PB), polybutylene terephthalate (PBT), polypropylene terephthalate (PPT), polyethylene naphthalate (PEN), polyhydroxyalkanoate (PHA), poly(methyl)methacrylate (PMMA) and polytrimethylene terephthalate (PTT).

Additionally, the material of the substrate may include copolymers made from the following monomers: acrylonitrile-butadiene-styrene (ABS), acrylonitrile-styrene-acrylate (ASA), ethylene-propylene (E/P), ethylene-vinyl acetate (EVAC), methyl methacrylate-acrylonitrile-butadiene-styrene (MABS), methacrylate-butadiene-styrene (MBS), melamine-formaldehyde (MF), melamine-phenol-formaldehyde (MPF), phenol-formaldehyde (PF), styrene-butadiene (SB), styrene-maleic anhydride (SMAH), copolyester thermoplastic elastomer (TPC), olefinic thermoplastic elastomer (TPO), styrenic thermoplastic elastomer (TPS), urethane thermoplastic elastomer (TPU), thermoplastic rubber vulcanisate (TPV), copolymer resins of styrene and acrylonitrile (SAN), styrene butadiene copolymer (SBC) and vinyl acetate-ethylene copolymer (VAE).

The advantageous properties of this invention can be observed by reference to the following examples, which illustrate, but do not limit, the invention.

EXAMPLES

Test Methods:

Method 1. Available chlorine determination: Available chlorine in the sample was analyzed by iodometric titration using a HACH® digital titrator. "Available chlorine" refers to the chlorine equivalent of the iodine liberated from potassium iodide when the hypochlorite solution is titrated with an acidic solution of sodium thiosulfate. A 100 ml beaker, equipped with a stir bar, was charged with 2 ml or 4 ml test samples. 50 ml deionized water was added to the beaker, and the solution was stirred at room temperature. The contents of a HACH® oxygen 3 powder pillow were immediately added to the beaker to lower the pH of the solution. Once the solids completely dissolved, the contents of one potassium iodide powder pillow were added to the beaker, which was then swirled to mix. This solution was then titrated with 2.00 N sodium thiosulfate solution until the solution was pale yellow. Approximately 1 ml of starch indicator solution was added to produce a dark blue solution, and the solution was further titrated with 2.00 N sodium thiosulfate until colorless. The titrator's digital readout was then recorded and converted first to total % (w/v) available chlorine and then to total % (w/w) available chlorine using the equations provided in formulae (II) and (III) below. In formula (II), the digit multiplier is 22.2 for 4 ml samples and 44.3 for 2 ml samples. The weight percent of sodium hypochlorite may then be determined according to formula (IV).

$$\text{Total available chlorine} (\% \text{ w/v, g/100 ml}) = \frac{\text{digits (digit multiplier)}}{10,000} \quad \text{(II)}$$

$$\text{Total available chlorine} (\% \text{ w/w}) = \frac{\% \text{ w/v available chlorine}}{\text{specific gravity}} \quad \text{(III)}$$

$$\text{NaOCl} (\% \text{ w/w}) = \% \text{ w/w available chlorine} \times 1.05 \quad \text{(IV)}$$

Method 2. Rapid stability study: A test sample, either as a spray solution or on a wipe, was placed in an incubator with a controlled temperature of 54±2° C. The sample remained in the incubator for 14 days and was then brought to room temperature. For wipe samples, liquid was expressed prior to any further analysis. The pH of the sample was determined according to standard methods, and the % available chlorine was determined in accordance with Method 1 above. A sample passes the test if a sample having an initial available chlorine content of 1.2% to 1.3% retains at least 0.95% available chlorine after 14 days incubation at 54±2° C. Alternatively, the sample passes if a sample having an initial available chlorine content of 1.0% retains at least 0.75% available chlorine after 14 days incubation at 54±2° C. Alternatively, the sample passes if a sample having an initial available chlorine content of 1.4% to 1.5% retains at least 1.0% to 1.1% available chlorine after 14 days incubation at 54±2° C.

Method 3. Antimicrobial efficacy evaluation: Two methods were used to determine an antimicrobial effectiveness index ("AEI"). Table 1 below correlates the percent reduction in microbial populations to a logarithmic reduction value, or AEI. As the AEI value increases, the amount of microbial kill events also increases. A sample is said to pass the antimicrobial efficacy test against *Mycobacterium terrae* if the AEI is greater than or equal to 4. The sample is said to pass the antimicrobial efficacy test against *C. diff.* spores if the AEI is greater than or equal to 6. It is noted that other jurisdictions may have differing efficacy requirements.

TABLE 1

| % reduction in microbial population | AEI |
|---|---|
| 90 | 1 |
| 99 | 2 |
| 99.9 | 3 |
| 99.99 | 4 |
| 99.999 | 5 |
| 99.9999 | 6 |

Method 3A. 96-well microtiter test (suspension test): The test substance was placed inside a well. The well was then inoculated with a suspension that contained the test organism and soil load. The contact time tested was equal to half the kill claim time. For instance, when the kill claim time was 3 minutes, the microbial suspension was exposed to the test substance for 1.5 minutes. The % reduction in microbial population was determined by colony counting, in colony-forming units (CFUs), at each dilution. This recorded value was used to calculate the $\log_{10}$ reduction (LR) in viable microorganisms, which is the difference between the mean $\log_{10}$ of the number of organisms in the control sample and the mean $\log_{10}$ of the number of organisms in the treated sample. If no microorganisms were recovered for any treated sample, LR is reported as greater than or equal to the mean $\log_{10}$ density for the control sample.

Method 3B. Quantitative disk carrier test (hard surface test): A suspension that contained the test organism and soil load was pipetted onto a stainless steel coupon. The suspension was then dried, and the test substance was deposited on the coupon for the required exposure time. The contact time tested was equal to the kill claim time. For instance, when the kill claim time was 3 minutes, the inoculated coupon was exposed to the test substance for 3 minutes. The % reduction in microbial population was determined by colony counting, in colony-forming units (CFUs), before and after treatment. This recorded value was used to calculate the LR in viable microorganisms, which is the difference between the mean $\log_{10}$ of the number of organisms in the untreated sample and the mean $\log_{10}$ of the number of organisms in the treated sample. If no microorganisms were recovered for any treated sample, LR is reported as greater than or equal to the mean $\log_{10}$ density for the untreated samples.

Exemplary formulation: To a vessel charged with purified water, sodium bicarbonate, sodium carbonate and concentrated sodium hypochlorite were added. The resulting solution was stirred until all solids dissolved. The final formulation consisted of 86.1 wt. % water, 0.3 wt. % sodium bicarbonate, 2.4 wt. % sodium carbonate, and 11.2 wt. % concentrated sodium hypochlorite. The total available chlorine in this formulation was 1.2 wt. %. The pH ranged from 10.0-10.5, the specific gravity ranged from 1.04-1.06, and the liquid formulation possessed a chlorine-like odor. For tests involving the disinfectant on a substrate, this liquid formulation was applied to a 100% polyester substrate.

Results: Six samples were tested as ready to use sprays in accordance with the Methods provided above. Table 2 summarizes the identity of the six samples. Table 3 provides the test results of the antimicrobial efficacy evaluation against *Mycobacterium terrae* and the rapid stability test for the six samples.

TABLE 2

| Sample | pH | Buffer |
|---|---|---|
| Comparative A | 12.3 | —[1] |
| Comparative B | 12.1 | —[1] |
| Comparative C | 12.3 | No |
| Comparative D | 11.5 | No |
| Comparative E | 10.0-10.5 | No |
| A | 10.0-10.5 | Yes |

[1]Comparative A and Comparative B are commercially available compositions. The presence or absence of a buffer is unknown.

TABLE 3

| | Antimicrobial Efficacy Evaluation | | |
|---|---|---|---|
| Sample | AEI | Pass/Fail | Rapid stability |
| Comparative A | 1.0 | Fail | ND[2] |
| Comparative B | 1.5 | Fail | ND[2] |
| Comparative C | 0.5 | Fail | Pass |
| Comparative D | 2.0 | Fail | Pass |
| Comparative E | 4.0 | Pass | Fail |
| A | 4.0 | Pass | Pass |

[2]The stabilities of commercially-available Comparative A and Comparative B were not determined ("ND"). However, the samples were deemed qualitatively stable due to their commercial availability.

In the absence of a buffer, a 1.0%-1.3% hypochlorite solution at pH 10.0-10.5 is highly efficacious, as shown by the AEI of 4 for Comparative Sample E. However, stability is compromised at this pH range, as is shown in the rapid stability test results for Comparative Sample E. The addition of a buffer as in Sample A, however, maintains the efficacy of the sample, but also significantly improves the stability of the solution. By way of contrast, Comparative Samples A, B, C and D, although stable, are not efficacious against *Mycobacterium terrae*.

Additionally, the effect of the buffer system on stability and efficacy was examined. As shown in Table 4, three buffer systems, carbonate, phosphate, and borate, were examined at around pH 10 and around pH 10.5. both at about 1% available chlorine.

As shown in Table 4, at a 2 minute kill claim time, a hypochlorite formulation with either a carbonate or phosphate buffer at about pH 10 passed the antimicrobial efficacy evaluation against *Mycobacterium terrae*, but the hypochlorite formulation with borate buffer did not. Also, all three samples failed the antimicrobial efficacy evaluation at about pH 10.5 and a 2 minute kill claim time. However, at a 3 minute kill claim time, the sample with a phosphate buffer failed the antimicrobial efficacy evaluation at around pH 10.5. All remaining samples passed the antimicrobial efficacy evaluation. Similar results were obtained for the antimicrobial efficacy evaluation against *C. diff.* at a 3 minute kill claim time. This data confirms that lower pH's have increased efficacy, and potentially at faster kill times depending on the buffers system.

The samples using either carbonate or phosphate buffers also passed the rapid stability test at around pH 10 and around pH 10.5. However, the samples with the borate buffer failed the rapid stability test at both pH levels.

Additionally, the use of mixed buffer systems provided stable hypochlorite solutions in the pH 10.0-10.5 range.

Further testing of a carbonate/bicarbonate buffer system indicated that samples have an increased tendency to fail the rapid stability test when the pH is decreased to values below 10.0, and particularly to values below 9.9. Table 5 provides rapid stability test results for samples with an initial available chlorine content of 1.0%, while Table 6 provides rapid stability test results for samples with an initial available chlorine content of 1.2% to 1.3%.

TABLE 5

| | Initial pH | | | | | |
|---|---|---|---|---|---|---|
| | 8.6 | 9.0 | 9.4 | 9.9 | 10.0 | 10.5 |
| Buffer | Carbonate | Carbonate | Carbonate | Carbonate | Carbonate | Carbonate |
| Initial % $Cl_2$ | 1.01 | 1.00 | 1.01 | 1.00 | 1.01 | 1.01 |
| 14 days 54 ± 2° C. % $Cl_2$ | 0.07 Fail | 0.23 Fail | 0.48 Fail | 0.78 Pass | 0.75 Pass | 0.83 Pass |
| 14 days 54 ± 2° C. pH | 8.4 | 9.0 | 9.4 | 9.9 | 9.9 | 10.3 |

TABLE 4

| | | | | Antimicrobial efficacy against *M. terrae* | | | | Antimicrobial efficacy against *C. diff.* | | |
|---|---|---|---|---|---|---|---|---|---|---|
| | | | | 2 min. claim | | 3 min. claim | | 3 min. claim | | Rapid |
| Sample | Buffer | pH | % $Cl_2$ (w/v) | AEI | Pass/Fail | AEI | Pass/Fail | AEI | Pass/Fail | Stability |
| B | Carbonate | 10.0 | 1.01 | 5.0 | Pass | 4.5 | Pass | 6.2 | Pass | Pass |
| C | Phosphate | 10.1 | 0.97 | 5.0 | Pass | 4.5 | Pass | 6.7 | Pass | Pass |
| D | Borate | 10.1 | 0.94 | 3.5 | Fail | 4.0 | Pass | ND[1] | N/A[2] | Fail |
| E | Carbonate | 10.4 | 1.00 | 2.5 | Fail | 4.5 | Pass | 6.7 | Pass | Pass |
| F | Phosphate | 10.5 | 0.93 | 2.5 | Fail | 3.5 | Fail | ND | N/A | Pass |
| G | Borate | 10.5 | 0.92 | 1.0 | Fail | 4.0 | Pass | 6.4 | Pass | Fail |

[1]Not determined;
[2]Not applicable

TABLE 6

| | Initial pH | | | | | |
|---|---|---|---|---|---|---|
| | 8.7 | 8.9 | 9.4 | 9.9 | 10.0 | 10.5 |
| Buffer | Carbonate | Carbonate | Carbonate | Carbonate | Carbonate | Carbonate |
| Initial % $Cl_2$ | 1.26 | 1.26 | 1.26 | 1.26 | 1.29 | 1.29 |
| 14 days 54 ± 2° C. % $Cl_2$ | 0.07 Fail | 0.18 Fail | 0.47 Fail | 0.93 Fail | 1.02 Pass | 1.13 Pass |
| 14 days 54 ± 2° C. pH | 8.6 | 8.9 | 9.3 | 9.8 | 9.9 | 10.4 |

Specifically, Table 5 shows that samples with 1.0% hypochlorite solution at pH ranging from 8.6-9.4 failed the rapid stability test, retaining only 0.07-0.48% available chlorine after 14 days incubation, while a sample at pH of 9.9 passed the rapid stability test, retaining 0.78% available chlorine after 14 days incubation, just above the 0.75% requirement. Table 6 shows that samples with 1.26% hypochlorite solution at pH ranging from 8.7-9.4 also failed the rapid stability test, retaining only 0.07-0.47% available chlorine after 14 days incubation, while a sample at pH of 9.9 just barely failed, retaining 0.93% available chlorine after 14 days incubation, just shy of the 0.95% requirement.

Additional rapid stability testing is shown in Table 7 for 1.0% hypochlorite solutions in the 10.0-10.5 pH range, or above 11 pH, either with no buffer or with a phosphate (e.g., sodium phosphate) or borate (e.g., boric acid) buffer.

TABLE 7

| | Initial pH | | | | | | | |
|---|---|---|---|---|---|---|---|---|
| | 10.0 | 10.0 | 10.0 | 10.5 | 10.5 | 10.5 | 11.5 | 12.3 |
| Buffer | None | Phosphate | Borate | None | Phosphate | Borate | None | None |
| Initial % $Cl_2$ | 1.01 | 1.00 | 0.98 | 1.00 | 1.01 | 1.00 | 1.03 | 1.03 |
| 14 days 54 ± 2° C. % $Cl_2$ | 0.62 Fail | 0.77 Pass | 0.59 Fail | 0.68 Fail | 0.81 Pass | 0.59 Fail | 0.91 Pass | 0.96 Pass |
| 14 days 54 ± 2° C. pH | 9.5 | 10 | 10.1 | 9.6 | 10.5 | 10.5 | 11.3 | 12.2 |

Table 7 shows that solutions with pH of 11.5 or greater were stable regardless of the presence of a buffer, but as shown in Table 3 above, efficacy against *Mycobacterium* is not achieved. Table 7 further shows that at pH of 10.0-10.5, stability requires a buffer system. Tables 5-7 collectively show that the carbonate and phosphate buffers were effective at stabilizing the solution in the 10.0-10.5 pH range, while borate as the sole buffer was not effective. However, adjustment of the amount or type of borate, or use of borate in a mixed buffer system could provide a passing result.

In general, certain buffers may be effective for both efficacy and rapid stability, while other buffers may be more effective for efficacy than rapid stability, or vice versa. Therefore, as needed, a mixed buffer system can be used to achieve both efficacy and rapid stability. For example, a buffer system containing both a borate buffer and a phosphate buffer may be used. By way of further example, any combination of two or three or four of a carbonate, a phosphate, a silicate and a borate is contemplated. In accordance with embodiments of the invention, one skilled in the art can adjust the pH, the available chlorine content, the buffer system type, and the buffer system amount to achieve passing results for antimicrobial efficacy evaluation against *C. diff.* and *Mycobacterium*, as well as rapid stability.

In summary, a pH of 10.0-10.5 has been shown to be most likely to meet the requirements of both efficacy and rapid stability, particularly with carbonate and phosphate buffer systems. A pH in the range of 9.9 to less than 10.0, or in the range of above 10.5 to 11, may meet both criteria, depending on the type and amount of the buffer system. Below a pH of 9.9, rapid stability is unlikely to be achieved regardless of the buffer system. Above a pH of 11, while the solution is likely stable, efficacy against both *Clostridium difficile* spores and *Mycobacterium* is unlikely to be achieved.

The efficacy of these solutions was also studied against fungi, such as *Trichophyton mentagrophytes* and *Aspergillus brasiliensis*, and viruses, such as poliovirus type 1 and feline calicivirus, as well as other types of bacteria. In general hypochlorite solutions with 1% available chlorine, at a pH around 10.0-10.5, using either carbonate, phosphate, or borate buffers, were found efficacious against the fungi studied. Likewise, hypochlorite solutions with 1% available chlorine, at a pH around 10.5, using either carbonate or borate buffers, were found efficacious against the viruses studied. Additionally, these solutions were found to be efficacious against the following organisms: *Clostridium difficile* spores, *Staphylococcus aureus, Pseudomonas aeruginosa, Salmonella enteric, Burkholderia cepacia, Escherichia coli, Klebsiella pneumonia, Legionella pneumophila, Listeria monocytogenes, Serratia marcescens, Streptococcus pyogenes, Neisseria gonorrhoeae, Enterobacter cloacae*, Multidrug Resistant *Acinetobacter baumannii*, Carbapenem-resistant *Klebsiella pneumoniae*, Methicillin Resistant *Staphylococcus aureus*, Penicillin Resistant *Streptococcus pneumonia*, Vancomycin Resistant *Staphylococcus aureus*, Vancomycin Resistant *Enterococcus faecalis, Escherichia coli, Mycobacterium tuberculosis, Candida albicans, Aspergillus brasiliensis, Trichophyton mentagrophytes*, Adenovirus, Hepatitis A, Feline Calicivirus, Poliovirus, Rhinovirus, Enterovirus, Human Rotavirus, Herpes simplex virus, Human Coronavirus, Influenza A virus, Influenza B virus, Duck Hepatitis B virus, Bovine-Viral Diarrhea Virus Hepatitis C virus, Human Immunodeficiency Virus, Respiratory syncytial virus, and Canine Parvovirus.

In a further set of experiments, the liquid hypochlorite ready-to-use formulations were applied to 100% polyester substrates to generate hypochlorite bleach wipes. Tuberculocidal and sporicidal efficacies were determined from the expressed liquid from the wipes. Similarly, Comparative wipes were studied. The results from these tests are summarized in Table 8.

TABLE 8

| Sample | pH | Antimicrobial efficacy against M. terrae | | Antimicrobial efficacy against C. diff. | |
|---|---|---|---|---|---|
| | | AEI | Pass/Fail | AEI | Pass/Fail |
| Comparative F | 11.4 | 1.0 | Fail | 6.0 | Pass |
| Comparative G | 11.7 | 1.5 | Fail | 6.0 | Pass |
| H | 10.0-10.5 | 5.2 | Pass | 6.2 | Pass |

As is shown in Table 8, wipes containing a hypochlorite solution with 0.75%-1.0% available chlorine with an appropriate buffer capable of maintaining the pH level at 10.0-10.5 passed the antimicrobial efficacy evaluation against both *Mycobacterium terrae* and *C. diff*. However, the comparative wipes did not exhibit similar efficacy against *Mycobacterium terrae*.

Thus, in accordance with embodiments of the invention, a disinfectant comprises a source of chlorine, a buffer system, a pH adjuster, and a polar carrier, the disinfectant having a pH of 9.9-11 and activity against *Clostridium difficile* spores and *Mycobacterium* within a 3 minute kill time. In embodiments of the invention, the disinfectant kills at least 99.99% of *Clostridium difficile* spores and *Mycobacterium* within the 3 minute kill time. In accordance with other embodiments of the invention, the disinfectant kills at least 90% of the microbial population on a surface within the 3 minute kill time. In accordance with yet other embodiments of the invention, the disinfectant kills at least 99% of the microbial population on a surface within the 3 minute kill time. In accordance with still other embodiments of the invention, the disinfectant kills at least 99.9% of the microbial population on a surface, and specifically at least 99.99% of *Clostridium difficile* spores and *Mycobacterium*, within the 3 minute kill time.

In accordance with a further embodiment of the invention, a method of reducing microbial population on a surface is provided. The method comprises contacting the surface with the disinfectant of any embodiment described herein for a sufficient time to kill at least 90% of the microbial population on the surface, and most advantageously, at least 99.9% of the microbial population on the surface. An article of manufacture is further provided, such as a wipe product in which the disinfectant of any embodiment herein is absorbed on a carrier or substrate, which may be in the form of individual sheets or a continuous sheet with separation means, as discussed in further detail above.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. A disinfectant consisting of:
   a source of chlorine,
   a buffer system that is a mixture of sodium carbonate and sodium bicarbonate,
   a pH adjuster, and
   a polar carrier,
   wherein the pH adjuster is selected from the group consisting of lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, hydrohalic acid, sulfuric acid, nitric acid, and combinations thereof;
   wherein the buffer system and pH adjuster are present in the disinfectant at 0.5% to 10% by weight;
   wherein the available chlorine concentration of the disinfectant is 0.5% to 10%;
   wherein the pH of the disinfectant is 9.9-11; and
   wherein the disinfectant has activity against *Clostridium difficile* spores and *Mycobacterium* within a 3 minute kill time.

2. The disinfectant of claim 1, wherein the pH of the disinfectant is 10-10.5.

3. The disinfectant of claim 1, wherein the pH of the disinfectant is 10-10.7.

4. The disinfectant of claim 1, wherein the source of chlorine is selected from the group consisting of sodium hypochlorite, potassium hypochlorite, calcium hypochlorite, lithium hypochlorite, sodium dichloroisocyanurate, potassium dichloroisocyanurate, pentaisocyanurate, trichloromelamine, sulfondichloroamide, 1,3-dichloro-5,5-dimethyl hydantoin, N-chlorosuccinimide, N,N'-dichloroazodicarbonimide, N,N'-chloroacetylurea, N,N'-dichloro biuret, trichlorocyanuric acid, and combinations thereof.

5. The disinfectant of claim 1, wherein the source of chlorine is sodium hypochlorite.

6. The disinfectant of claim 1, wherein the pH adjuster is sodium hydroxide.

7. The disinfectant of claim 1, wherein the polar carrier is water.

8. The disinfectant of claim 1, wherein the disinfectant is absorbed on a substrate.

9. The disinfectant of claim 8, wherein the substrate is selected from the group consisting of polyethylene terephthalate, polyester, high density polyethylene, polyvinyl chloride, chlorinated polyvinylidene chloride, polyacrylamide, polystyrene, polypropylene, polycarbonate, polyaryletherketone, poly(cyclohexylene dimethylene cyclohexanedicarboxylate), poly(cyclohexylene dimethylene terephthalate), poly(cyclohexylene dimethylene terephthalate) glycol, polyetherimide, polyethersulfone, poly(ethylene terephthalate) glycol, polyketone, poly(oxymethylene); polyformaldehyde, poly(phenylene ether), poly(phenylene sulfide), poly(phenylene sulfone), syndiotactic polystyrene, polysulfone, polytetrafluoroethylene, polyurethane, poly(vinylidene fluoride), polyamide thermoplastic elastomer, polybutylene, polybutylene terephthalate, polypropylene terephthalate, polyethylene naphthalate, polyhydroxyalkanoate, poly(methylmethacrylate), and polytrimethylene terephthalate.

10. The disinfectant of claim 8, wherein the substrate is a copolymer selected from the group consisting of acrylonitrile-butadiene-styrene, acrylonitrile-styrene-acrylate, ethylenepropylene, ethylene-vinyl acetate, methyl methacrylate-acrylonitrile-butadiene-styrene, methacrylate-butadiene-styrene, melamine-formaldehyde, melamine-phenol-formaldehyde, phenol-formaldehyde, styrene-butadiene, styrene-maleic anhydride, copolyester thermoplastic elastomer, olefinic thermoplastic elastomer, styrenic thermoplastic elastomer, urethane thermoplastic elastomer, thermoplastic rubber vulcanisate, copolymer resins of styrene and acrylonitrile, styrene butadiene copolymer, and vinyl acetate-ethylene copolymer.

11. The disinfectant of claim 8, wherein the substrate is polyester.

12. The disinfectant of claim 1, wherein the disinfectant kills at least 99.99% of *Clostridium difficile* spores and *Mycobacterium* within a 3 minute kill time.

13. A disinfectant consisting of:
sodium hypochlorite as a source of chlorine,
a carbonate buffer system,
a hydroxide pH adjuster, and
a polar carrier,
wherein the hydroxide pH adjuster is selected from the group consisting of lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, and combinations thereof;
wherein the carbonate buffer system and hydroxide pH adjuster are present in the disinfectant at 0.5% to 10% by weight;
wherein the available chlorine concentration of the disinfectant is 0.5% to 10%;
wherein the pH of the disinfectant is 10.0-10.5; and
wherein the disinfectant kills at least 90% of *Clostridium difficile* spores and *Mycobacterium* within a 3 minute kill time.

14. The disinfectant of claim 13, wherein the carbonate buffer system is a mixture of sodium carbonate and sodium bicarbonate.

15. The disinfectant of claim 13, wherein the disinfectant is absorbed on a substrate.

16. The disinfectant of claim 15, wherein the substrate is polyester.

17. The disinfectant of claim 13, wherein the disinfectant kills at least 99% of *Clostridium difficile* spores and *Mycobacterium* within the 3 minute kill time.

18. The disinfectant of claim 13, wherein the disinfectant kills at least 99.9% of *Clostridium difficile* spores and *Mycobacterium* within the 3 minute kill time.

19. The disinfectant of claim 13, wherein the disinfectant kills at least 99.99% of *Clostridium difficile* spores and *Mycobacterium* within the 3 minute kill time.

20. The disinfectant of claim 19, wherein the disinfectant kills at least 99.999% of *Clostridium difficile* spores within the 3 minute kill time.

21. The disinfectant of claim 19, wherein the disinfectant kills at least 99.9999% of *Clostridium difficile* spores within the 3 minute kill time.

22. A method of reducing microbial population on a surface, comprising contacting the surface with the disinfectant of claim 1 for a time equal or less than 3 minutes to kill at least 90% of the microbial population on the surface.

23. A disinfectant article comprising:
an absorbent carrier and a disinfectant absorbed on the absorbent carrier,
wherein the disinfectant consists of:
a source of chlorine,
a buffer system that is a mixture of sodium carbonate and sodium bicarbonate,
a pH adjuster, and
a polar carrier,
wherein the pH adjuster is selected from the group consisting of lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, hydrohalic acid, sulfuric acid, nitric acid, and combinations thereof;
wherein the buffer system and pH adjuster are present in the disinfectant at 0.5% to 10% by weight;
wherein the available chlorine concentration of the disinfectant is 0.5% to 10%;
wherein pH of the disinfectant is 9.9-11; and
wherein the disinfectant has activity against *Clostridium difficile* spores and *Mycobacterium* within a 3 minute kill time.

24. The disinfectant article of claim 23, wherein the absorbent carrier is a continuous sheet that includes partial tears or perforations that subdivide the absorbent carrier into individual wipes.

* * * * *